(12) United States Patent
Yang et al.

(10) Patent No.: US 12,275,987 B2
(45) Date of Patent: Apr. 15, 2025

(54) EGG-TYPE CHICKEN WHOLE-GENOME SNP CHIP AND USE THEREOF

(71) Applicant: China Agricultural University, Beijing (CN)

(72) Inventors: Ning Yang, Beijing (CN); Congjiao Sun, Beijing (CN); Zhuang Liu, Beijing (CN); Yiyuan Yan, Beijing (CN); Guiqin Wu, Beijing (CN)

(73) Assignee: China Agricultural University, Beijing (CN)

( * ) Notice: Subject to any disclaimer, the term of this patent is extended or adjusted under 35 U.S.C. 154(b) by 1053 days.

(21) Appl. No.: 17/281,223

(22) PCT Filed: Sep. 29, 2018

(86) PCT No.: PCT/CN2018/108741
§ 371 (c)(1),
(2) Date: Mar. 29, 2021

(87) PCT Pub. No.: WO2020/062160
PCT Pub. Date: Apr. 2, 2020

(65) Prior Publication Data
US 2021/0395803 A1 Dec. 23, 2021

(51) Int. Cl.
*C12Q 1/68* (2018.01)
*C12N 15/10* (2006.01)
*C12Q 1/6827* (2018.01)
*C12Q 1/6837* (2018.01)
*C12Q 1/6876* (2018.01)

(52) U.S. Cl.
CPC ....... *C12Q 1/6837* (2013.01); *C12N 15/1065* (2013.01); *C12Q 1/6827* (2013.01); *C12Q 1/6876* (2013.01); *C12Q 2600/124* (2013.01); *C12Q 2600/156* (2013.01)

(58) Field of Classification Search
None
See application file for complete search history.

(56) References Cited

FOREIGN PATENT DOCUMENTS

CN 105238859 B 3/2018

OTHER PUBLICATIONS

Liu Wenbo et al., Screening of Polymorphic Loci Associated with Eggshell Quality Traits Using High-Density SNP Chips, College of Animal Science and Technology, China Agricultural University, Beijing 100193 (non-official translation: The 16th National Conference on Animal Genetics and Breeding Academic Discussions, Dec. 11, 2011) (2 pgs.).

*Primary Examiner* — Jeanine A Goldberg
(74) *Attorney, Agent, or Firm* — Westbridge IP LLC

(57) ABSTRACT

Provided are an egg-type chicken whole-genome SNP chip and the use thereof. The SNP loci of the chip are respectively derived from 14,624 SNP loci shared by each line of the major egg-type chickens in China; 3,677 SNP loci associated with disease-resistant traits in egg-type chickens; 16,000 SNP loci associated with economic traits in egg-type chickens; and 9,358 SNP loci making up genomic regions not covered by the foregoing probes. The 43,681 SNPs on the egg-type chicken whole-genome SNP chip have DNA sequences as represented by SEQ ID NO. 1-43,681. The chip can specifically identify the genetic relationship between commercial egg-type chickens and egg-type chickens of local breeds, and can also perform applications such as whole-genome association analysis, genome selective breeding, and QTL location analysis of target traits and population genetic analysis.

1 Claim, 4 Drawing Sheets
Specification includes a Sequence Listing.

EGG-TYPE CHICKEN WHOLE-GENOME SNP CHIP AND USE THEREOF

RELATED APPLICATIONS

This application is a national stage filing under 35 U.S.C. § 371 of International Patent Application No. PCT/CN2018/108741, filed Sep. 29, 2018, which is incorporated by reference herein in its entirety.

TECHNICAL FIELD

The present invention relates to the fields of molecular biology, functional genomics, bioinformatics and genome breeding, and more particularly relates to a whole-genome SNP chip for egg-type chicken and use thereof.

BACKGROUND ART

SNP refers to polymorphism of a nucleic acid sequence caused by the change of a single nucleotide base at the genome level. Its mutation forms include conversion, transversion, deletion and insertion and the like and SNP has the characteristics of large number, wide distribution and easy detection. As a genetic marker, SNP contributes to the genetic variation of qualitative and quantitative traits, and also some complex disease traits, so it is widely used in genetic research. A SNP chip is made by fixing a large number of fluorescently labeled DNA probes on a glass substrate through photoetching. It works by means of hybridizing and binding the probe DNA strand with the test target genomic DNA, and after staining with a dye, using a laser for scanning to perform genotyping of SNPs. The advantages of the SNP biochip lie in that the detection throughput is very large, and it can detect hundreds of thousands or even millions of SNP loci at a time with high detection accuracy.

A whole-genome SNP chip is a single nucleotide polymorphism (SNP) microarray, with millions of DNA marker sequences aligned and immobilized to form an array of SNP probes on a glass slide or a special silicon wafer. It works by means of base-pairing reaction between the DNA marker sequences immobilized on the chip and the target genome so as to accurately identify the genetic information. The SNP chip uses advanced microbiochemical reaction technology, micro-labeling technology, imaging technology with micro-scale scanning resolution and biological information computer processing technology to accurately identify specific mRNA or DNA sequences in biological individuals. There are two main commercial chicken SNP chips, Illumina's iSelect chicken 60K SNP chip (which is off the shelf and owned by Cobb, USA) and Affymetrix's 600K high-density chip. The Affymetrix 600K SNP chip currently on the market includes about 560,000 SNPs, and SNP loci are mainly derived from commercial broiler lines, egg-type chicken lines and some inbred lines. Compared with the previous Illumina 60K chip, the chip density of Affymetrix 600K SNP chip has been greatly improved, but the application of these SNP loci in Chinese local breeds has not achieved the desired effect. From the applicant's previous test results (about 2,600 chicken individuals), it is found that about half of the SNP loci on the Affymetrix 600K high-density SNP chip have poor polymorphism, and the high cost has further hindered its practical application in large-scale populations in China.

The livestock and poultry whole-genome SNP chip can be applied to many aspects such as molecular genetic research, molecule-assisted breeding and the like due to its advantages such as high marker density, uniform coverage of the whole genome, high measurement accuracy, easy realization of standardization and automated detection, etc. It can provide support for upstream and downstream processes of breeding, including genetic diversity analysis of germplasm resources, genetic relationship analysis, whole-genome association analysis, QTL (quantitative trait locus) mapping, selection and evolution studies and the like, wherein its application in genomic selection is very important. Genomic selection is currently the main breeding technique in livestock and poultry breeding, which uses whole-genome markers to estimate all possible genetic effects, interpret all genetic variations, and predict Genomic Breeding Values by adding up the genetic effects of markers. Genomic selection has the advantages of high accuracy of estimated breeding values and rapid genetic progress and has been applied to the breeding practice of commercialized lines of dairy cows, pigs, abroad high-yielding egg-type chickens and fast growing white-feather broilers.

However, the loci information of the current chicken 600K commercial SNP chip (Axiom® Genome-Wide Chicken Genotyping Array) lacks the genome variation information of Chinese local chicken breeds, and there are great limitations in its application in Chinese local chicken breeding and related basic scientific research. Moreover, compared with other animals, chickens have the characteristics of numerous breeds and large population, low individual price and the like, and therefore, a relatively low-cost whole-genome SNP chip is needed for large population sample testing. Thus, in egg-type chicken breeding industry and scientific research fields, it is urgently needed to develop a whole-genome SNP chip with moderate throughput, including specific information about the genetic variations of Chinese local egg-type chicken breeds.

SUMMARY OF THE INVENTION

One purpose of the present invention is to provide a whole-genome SNP chip for egg-type chicken and use thereof.

The present invention first provides a combination of whole-genome SNP markers consisting of 43,681 SNP loci, the nucleotide sequences of which are represented by SEQ ID NOs. 1 to 43681, respectively.

The present invention provides an egg-type chicken whole-genome SNP chip comprising 43,681 SNP molecular markers having the nucleotide sequence represented by SEQ ID NOs. 1 to 43681.

In the egg-type chicken whole-genome SNP chip provided by the present invention, SNP loci include five types of probes: the first type of probes are well-polymorphic SNP loci including 14,624 loci and screened from resequencing data of a total of 479 individuals of 7 domestic lines in China (Line 1 derived from Rhode Island Red, Line 2 and 3 derived from Rhode Island White, Line 4 and Line 5 derived from White Leghorn, Line 6 derived from Houdan, and Line 7 derived from Dongxiang blue-egg shell chicken); the second type of probes relate to the functional loci discovered by the applicant in the early research on disease-resistant traits of egg-type chickens, and include 3,677 SNPs; the third type of probes include significant loci related to important economic traits (laying performance, egg quality, feed efficiency and the like) of egg-type chickens which was excavated by the applicant through genome-wide association analysis (GWAS) technology, and include a total of 2,677 SNPs; the fourth type of probes include loci related to the economic traits of egg-type chickens reported in the literature of relevant candidate genes and QTL database, and include a total of 13,345 SNPs; and the fifth type of probes include 9,358 SNP loci from the SNP database (ftp.ncbi.nlm.nih.gov/snp/organisms/archive/chicken_9031/) which supplement the areas that the previous types failed to cover. The above five types of probes include a total of 43,681 SNP loci.

In the combination of egg-type chicken whole-genome SNP molecular markers and the egg-type chicken whole-genome SNP chip according to the present invention, the SNP loci of the molecular markers are located at the $61^{st}$ position of the nucleotide sequences represented by SEQ ID NOs. 1 to 43681.

The molecular markers are associated with disease-resistant traits in chickens or associated with economic traits in egg-type chickens. The disease-resistant trait is a trait resistant to Marek's disease; and the economic traits are laying performance, egg quality, feed reward and immunity.

The present invention also provides use of the above-mentioned egg-type chicken whole-genome SNP chip in the detection of DNA samples. The chip can be used in applications such as evaluation of germplasm resources for hen breed resources, genomic selection, identification of QTLs for target traits, association loci and candidate genes, genetic relationship identification and the like.

Specifically, the present invention provides the use of the above-mentioned combination of egg-type chicken whole-genome SNP molecular makers and/or the above-mentioned egg-type chicken whole-genome SNP chip in improving egg-type chicken germplasm resources.

The present invention provides the use of the above-mentioned combination of egg-type chicken whole-genome SNP molecular markers and/or the above-mentioned egg-type chicken whole-genome SNP chip in identifying breeds of egg-type chickens.

The present invention provides the use of the above-mentioned combination of egg-type chicken whole-genome SNP molecular markers and/or the above-mentioned egg-type chicken whole-genome SNP chip in genomic selection of egg-type chicken.

The present invention provides the use of the above-mentioned combination of egg-type chicken whole-genome SNP molecular markers and/or the above-mentioned egg-type chicken whole-genome SNP chip in identifying genetic relationship between chicken breeds or lines.

The present invention provides the use of the above-mentioned combination of egg-type chicken whole-genome SNP molecular markers and/or the above-mentioned egg-type chicken whole-genome SNP chip in analyzing genetic diversity of egg-type chicken.

The present invention provides the use of the above-mentioned combination of egg-type chicken whole-genome SNP molecular markers and/or the above-mentioned egg-type chicken whole-genome SNP chip in QTL mapping for target traits of egg-type chickens.

All SNP markers on the egg-type chicken whole-genome SNP chip of the present invention are named according to the name in the SNP database, the nucleotide sequences of which are derived from the $5^{th}$ version chicken reference genome (Gallusgallus-5.0, 2016).

The advantages of the present invention lie in that: 1). optimized design: even distribution on each chromosome of the whole-genome with high coverage, which ensures the accuracy of genetic evaluation of the egg-type chicken genome; 2). functional correlation: the significant loci related to traits such as laying performance, disease-resistant traits, feed utilization efficiency and egg quality of egg-type chickens are collected in the chip, and the practicability of the chip is increased; and 3). applicability: the chip loci are derived from SNPs with high polymorphism in independently bred commercial high-yielding egg-type chicken breeds and Chinese local chicken breeds, which not only meets the scientific research needs of scientific researchers, but also satisfies requirements of the whole genome molecular breeding work of egg-type chicken companies.

SPECIFIC MODES FOR CARRYING OUT THE EMBODIMENTS

Figure 1:
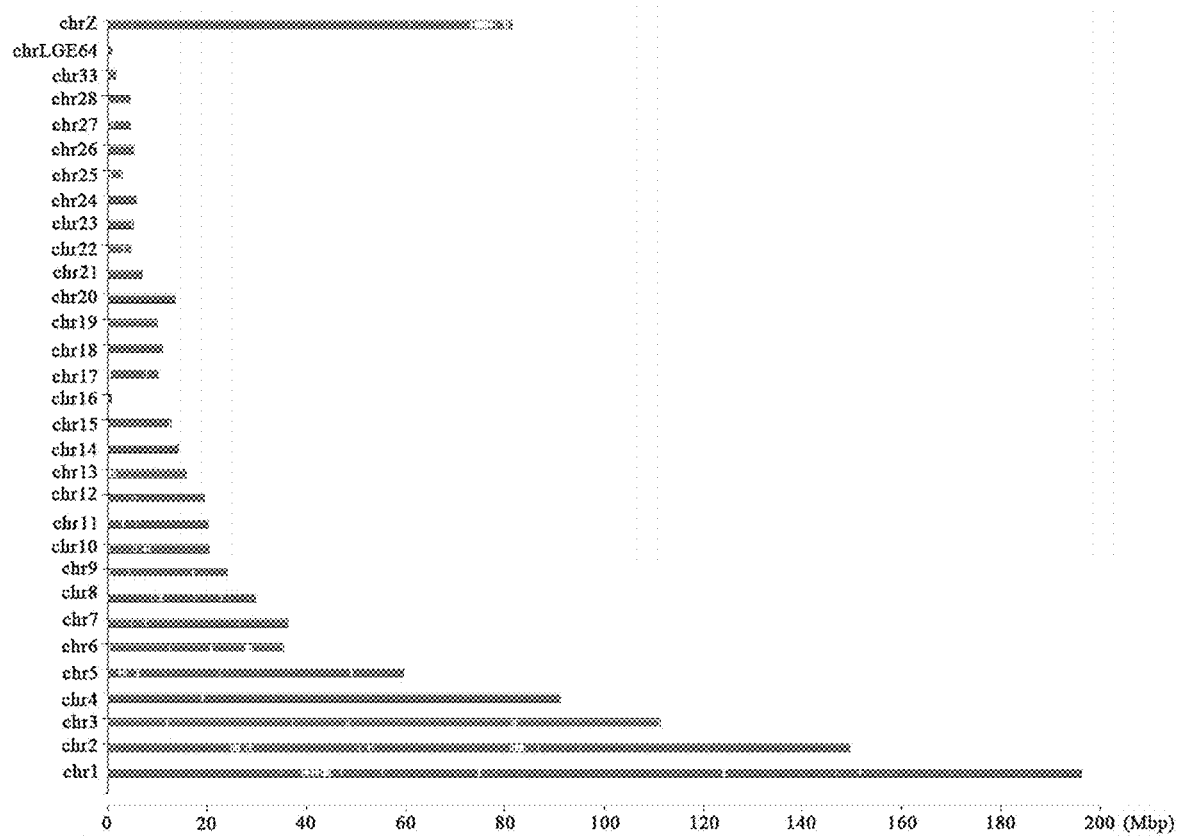
FIG. 1 shows the distribution in the chicken genome of the egg-type chicken whole-genome SNP chip in the present application. The abscissae represent 20, 40, 60, 80, 100, 120, 140, 160, 180, 200 Mb, respectively, and the ordinates represent chr1, chr2, chr3, chr4, chr5, chr6, chr7, chr8, chr9, chr10, chr11, chr12, chr13, chr14, chr15, chr16, chr17, chr18, chr19, chr20, chr21, chr22, chr23, chr24, chr25, chr26, chr27, chr28, chr33, chrLGE64 and chrZ from bottom to top.

The following Examples further illustrate the content of the present invention, but should not be construed as limiting the present invention. Without departing from the spirit and essence of the present invention, any modifications or replacements made to the methods, steps or conditions of the present invention fall within the scope of the present invention.

Unless otherwise specified, the technical means used in the Examples are conventional means well known to a person skilled in the art.

Example 1: Preparation Method of Egg-Type Chicken Whole-Genome SNP Chip

The first type of probes of the present invention were obtained as follows: commercial egg-type chicken breeds independently bred in China and Chinese local egg-type chicken breeds were subjected to the whole-genome resequencing, wherein, the egg-type chickens include 7 lines (Line 1 derived from Rhode Island Red, Line 2 and 3 derived from Rhode Island White, Line 4 and Line 5 derived from White Leghorn, Line 6 derived from Houdan, and Line 7 derived from Dongxiang blue-egg shell chicken), totally 479 individuals (Line 1: 92, Line 2: 74, Line 3: 91, Line 4: 60, Line 5: 69, Line 6: 68, and Line 7: 25), the SNP loci of each breed with MAF<0.05 were eliminated, and at the same time the SNPs shared by each line and the SNP loci shared by Line 1 and at least one other lines were screened out, which guarantees the polymorphism and versatility of SNP loci to a large extent. Finally, 64,396 SNPs shared by all lines and 3,782,699 SNP loci shared by Line 1 and any other lines were used as the core candidate SNPs of the chip.

The second type of probes of the present invention were obtained as follows: based on the applicant's earlier research on disease-resistant traits of chickens, using the Marek's disease-resistant inbred White Leghorn population established by the Poultry Disease and Tumor Laboratory of the United States Department of Agriculture (wherein, there are three individuals each for the disease-resistant line and the susceptible line). Through whole-genome resequencing technology, the genetic variations existing in each line is unearthed, and a total of 1,554,188 specific SNP loci of the lines related to disease-resistant traits were selected, and then subjected to overlapping with the SNPs with good polymorphism obtained by resequencing of 479 individuals in the 7 lines described in the previous step of preparation of the first type of probes, which greatly guarantees the applicability of these SNP loci in other egg-type chicken breeds. Finally, 480,341 disease-resistant specific SNPs were selected.

The third type of probes of the present invention were obtained as follows: this type of probes were obtained by screening based on the applicant's previous genome-wide association analysis of important economic traits in egg-type chickens. There are two parts: the first part comprises performing association analysis on laying performance (number of eggs laid and egg weight) and egg quality using 385 White Leghorns and 361 Dwarf egg-type chickens from 40 families; and the second part comprises performing whole-genome association analysis on laying performance, feed utilization efficiency, egg quality and reproductive performance of 1,512 hens which are F2 resource population obtained by the reciprocal cross between White Leghorn and Dongxiang blue-egg shell egg-type chicken. The above obtained SNP loci associated with important economic traits in egg-type chickens were analyzed and deduplicated by biostatistics methods, and 2,677 functional loci were obtained and added to the chip.

The fourth type of probes of the present invention were obtained as follows: QTLs related to egg quality, laying performance, feed efficiency and immunity of the chickens were obtained by searching for related candidate genes in published literature and online QTL database (www.animalgenome.org/cgi-bin/QTLdb/GG/index), QTLs with large confidence intervals and insignificant P values (P>0.05) were eliminated, and 1,238 candidate QTL intervals were finally obtained, then SNPs obtained from resequencing data were subjected to overlapping with candidate genes and QTLs, so as to screen out 589,164 SNPs as candidate loci related to traits.

The fifth type of probes of the present invention were obtained by downloading from the chicken SNP database of NCBI (www.ncbi.nlm.nih.gov/snp).

Identification process of SNP loci: considering that the sizes of different chromosome fragments in chickens are quite different, and the recombination rates of mutation loci on different chromosomes are inconsistent, the level of linkage disequilibrium on each chromosome was firstly detected, so as to set the optimal window/interval size for each chromosome, these windows/intervals were used to make SNPs evenly distributed on each chromosome, and one SNP shared by each line of the first type of probe was preferentially selected for each interval. If there was less than one, the SNP of the second type of probe was selected. The third type of probes were SNPs that were forced to be placed in the chip. If the window cannot be covered after the first type of probes and the second type of probes were selected, the SNP of the fourth type of probes was selected, and the fifth type of probes were used to supplement the interval that cannot be covered by the above-mentioned types of probes.

Figure 2:
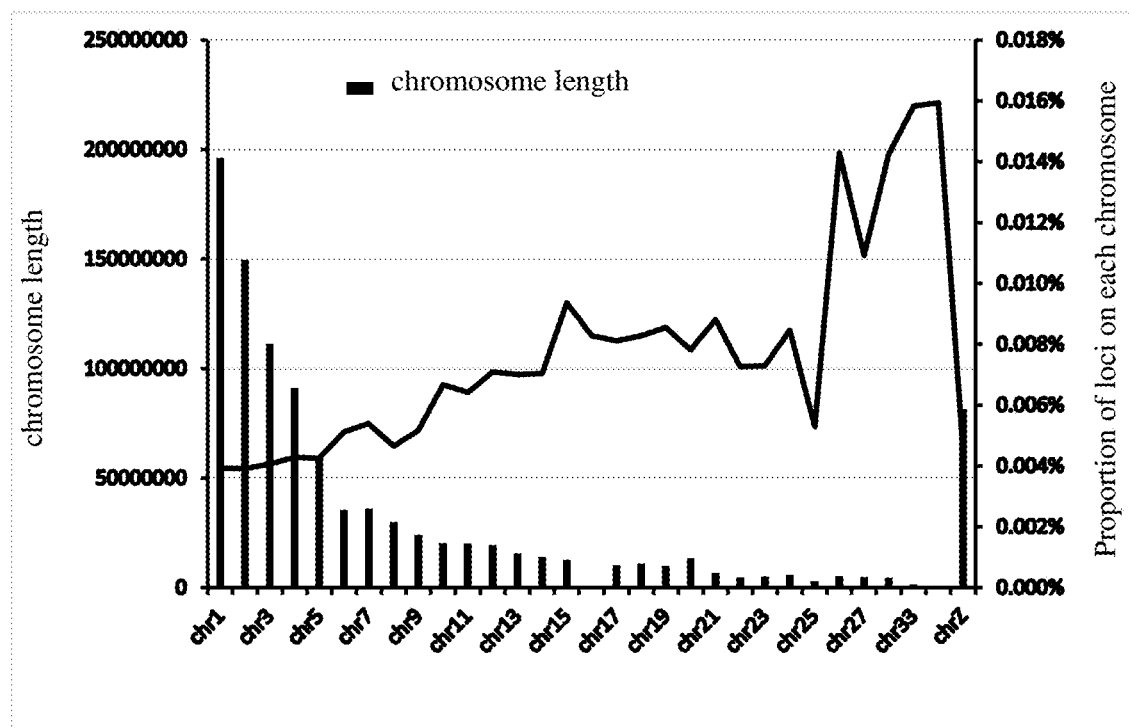
FIG. 2 shows the proportion of all SNP loci on each chromosome of the whole-genome in the present application.

The identified SNP loci were submitted to Illumina for scoring with the Infinium XT scoring system (www.illumina.com/), and all loci with scores less than 0.8 were removed. For the deleted unqualified SNP loci, the nearest SNP loci were selected for supplementation, and the scoring was performed again. According to the above steps for identification and screening, a total of 50,000 tag-SNP loci were obtained. Since there is a problem of successful conversion rate when making a chip with these 50,000 SNP loci by the Illumina Infinium XT platform, thus, the number of effective SNP loci on the final egg-type chicken whole-genome 50K SNP chip is 43,681 (see FIG. 1 and FIG. 2).

TABLE 1

The distribution number of loci of the egg-type chicken whole-genome SNP chip of the present invention on each chromosome

| Chromosome | length (bp) | number |
|---|---|---|
| chr1 | 196,202,544 | 6,916 |
| chr2 | 149,560,735 | 5,111 |
| chr3 | 111,302,122 | 3,907 |
| chr4 | 91,282,656 | 3,419 |
| chr5 | 59,825,302 | 2,287 |
| chr6 | 35,467,016 | 1,604 |
| chr7 | 36,946,936 | 1,722 |
| chr8 | 29,963,013 | 1,248 |
| chr9 | 24,091,566 | 1,117 |
| chr10 | 20,435,342 | 1,227 |
| chr11 | 20,218,793 | 1,148 |
| chr12 | 19,948,154 | 1,213 |
| chr13 | 18,407,460 | 973 |
| chr14 | 15,595,052 | 861 |
| chr15 | 12,762,846 | 994 |
| chr16 | 652,338 | 47 |
| chr17 | 10,956,400 | 718 |
| chr18 | 11,053,727 | 799 |
| chr19 | 9,979,828 | 735 |
| chr20 | 14,409,371 | 915 |
| chr21 | 6,862,722 | 513 |
| chr22 | 4,729,743 | 300 |
| chr23 | 5,786,528 | 313 |
| chr24 | 6,280,547 | 439 |
| chr25 | 2,906,300 | 131 |
| chr26 | 5,313,770 | 654 |
| chr27 | 5,655,794 | 441 |
| chr28 | 4,974,273 | 524 |
| chr32 | 78,254 | 13 |
| chr33 | 1,648,031 | 201 |
| chrLGE64 | 897,576 | 109 |
| chrZ | 82,310,166 | 3,082 |
| Total | | 43,681 |

Figure 3:
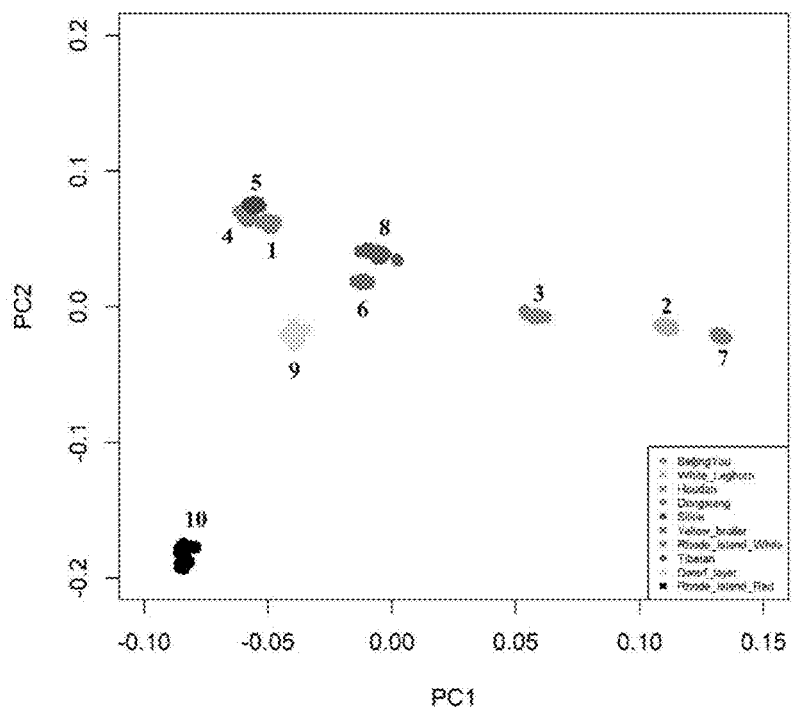
FIG. 3 shows the principal component analysis diagram of each chicken breed. The numbers in the figure represent 10 breeds, respectively. 1 represents Beijing You chicken, 2 represents White Leghorn, 3 represents Houdan, 4 represents Dongxiang blue-egg shell egg-type chicken, 5 represents Silkie, 6 represents Yellow broiler, 7 represents Rhode Island white, 8 represents Tibetan chicken, 9 represents Dwarf chicken, and 10 represents Rhode Island Red.
Figure 4:
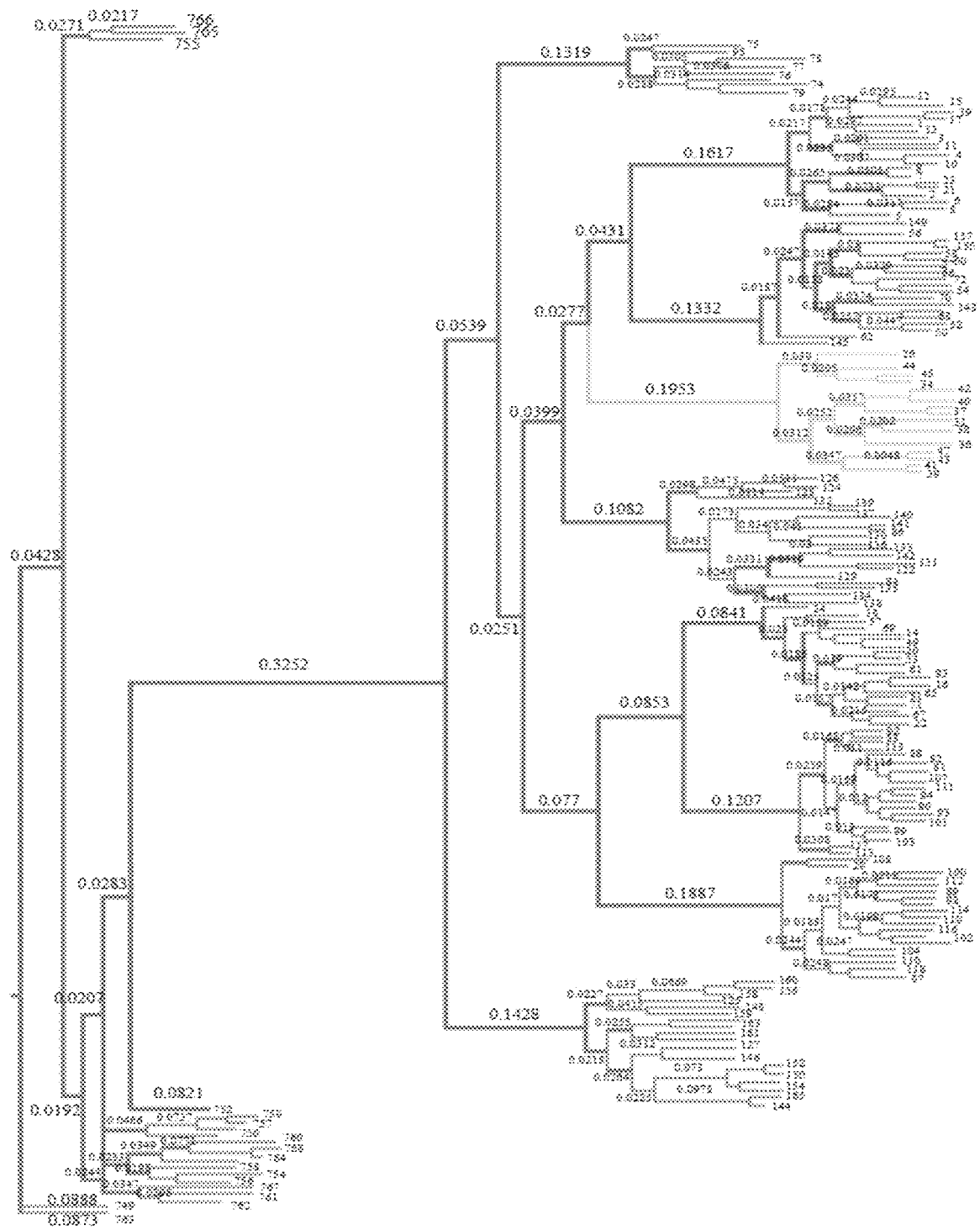
FIG. 4 shows the cluster analysis diagram of each chicken breed. The large branches represent that each breed can be distinguished independently, and the small branches represent each individual.

Example 2: Principal Component and Cluster Analysis Based on the Egg-Type Chicken Whole-Genome SNP Chip of the Present Invention DNA genotypes of 20 Rhode Island Red, 20 Rhode Island white, 19 Beijing You chickens, 19 White Leghorn, 19 Houdan, 20 Dongxiang blue-egg shell egg-type chickens, 20 Silkie, 8 Yellow broilers, 20 Tibetan chickens, and 20 Dwarf chickens were detected by using the the whole-genome of egg-type chicken 50K SNP chip provided by the present invention. After the SNP loci with MAF less than 0.01 (641 SNP loci) were firstly eliminated, principal component and cluster analysis were performed with PLINK and SNPhylo software, respectively. The results of principal component analysis and clustering evolutionary tree analysis were shown in FIGS. 3 and 4. All breeds can be distinguished separately, which also illustrates the applicability of the chip of the present invention in different breeds. Among them, the local breeds of Beijing You chickens, Dongxiang and Silkie are clustered into one group, the abroad commercial breeds of Rhode Island White, White Leghorn and Houdan are clustered into one group, and in particular, Rhode Island Red chickens are individually clustered into one group with a genetic distance far from other breeds. This is also because Rhode Island Red has undergone high-intensity artificial selection for multiple generations, and the genetic structure of the genome and nucleic acid polymorphisms have changed. The above-mentioned principal component and cluster analysis results can well prove the applicability of the chip, and the identification results are accurate and reliable.

Figure 5:
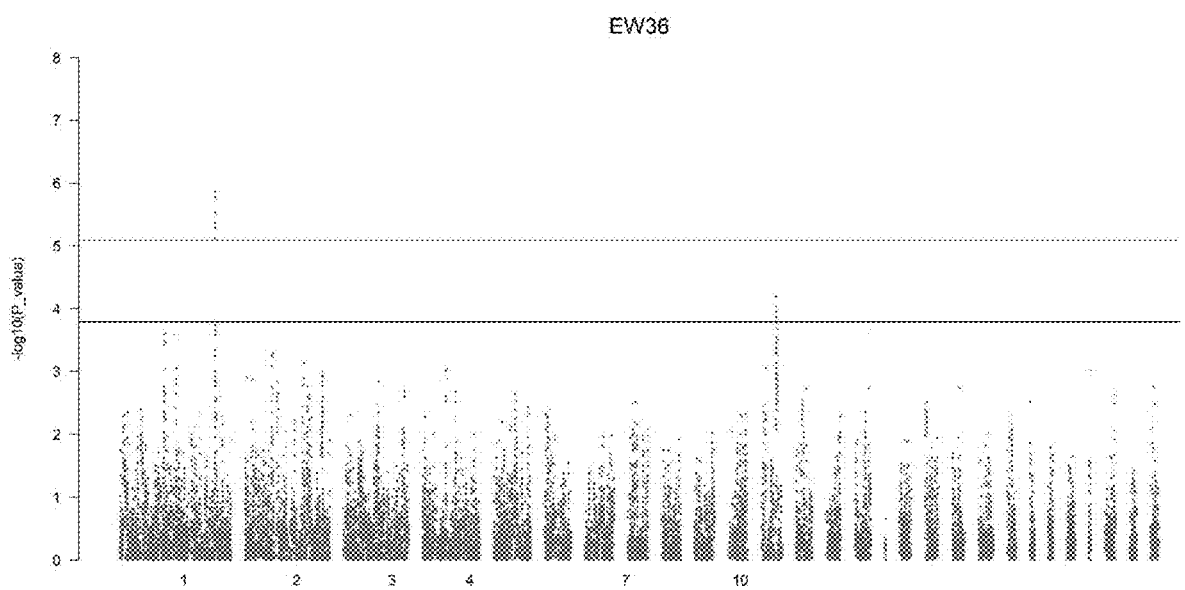
FIG. 5 shows the Manhattan graph of the egg weight of 36-week-old Rhode Island Red.

Example 3: Application of the Whole-Genome SNP Chip of the Present Invention in Genome-Wide Association Analysis 680 Rhode Island Red hens provided by Beijing Huaduyukou Poultry Co., Ltd were subjected to genotype detection using the egg-type chicken whole-genome SNP chip provided by the present invention, at the same time, the egg weight phenotype data of these hens at 36 weeks of age (EW36) were collected, and the quality control standards for SNP genotyping were as follows: sample Call rate>95%, MAF>0.01, and Hardy-Weinberg equilibrium test P value is less than 1e-06. After quality control, the remaining 673 individuals and 38,627 SNPs were used for the following genome-wide association (GWAS) analysis. Linear Mixture Model was used as the analyzing model, the P values of 8.1e-06 and 1.62e-04 in number of independent test of SNP were respectively used as the thresholds for genome-wide significance and potential genome-wide significance. The Manhattan graph of the GWAS results was shown in FIG. 5. The results show that there is a significant region associated with egg weight on chromosome 1, which is also consistent with the results reported in previous studies (Liu et al., 2018, Frontiers in Genetics).

Example 4: Use of the Egg-Type Chicken Whole-Genome SNP Chip of the Present Invention in Genomic Selection—Genetic Evaluation The egg-type chicken whole-genome SNP chip provided by the present invention was used for genetic evaluation of the genome. The DNA of 2,950 egg-type chickens (285 roosters and 2,665 hens) of three generations of a certain line provided by Beijing Huaduyukou Poultry Industry Co., Ltd were subjected to SNP genotyping. At the same time, genetic evaluation of the body weight at 28 weeks of age (BW28), the egg weight of hens at 28 weeks of age (EW28), and the number of eggs laid at 38 weeks of age (EN38) of these individuals were performed using both pedigree-based selection methods and genome-based selection methods. The specific steps were as follows:
(1) The typing test results of 2,950 chickens were subjected to quality control, the sample Call rate>95%, MAF>0.01, and Hardy-Weinberg equilibrium test P value is less than 1e-06. After quality control, the remaining 2,950 individuals and 38,413 qualified SNPs were used for genome-wide selection analysis.
(2) Model: BW28=Date+Hatch+Sex+Animal+Error
EW28/EN38=Date+Hatch+Animal+Error
Date, Hatch, and Sex are the fixed effects of individual birth date, hatching batch, and gender, respectively;
Animal is the random additive genetic effect of an individual animal, that is, individual's breeding value.
Error is random residual.
(3) Genetic evaluations were performed by pedigree-based selection method (PBLUP model) and genome-based selection method (ssGBLUP: one-step genomic model).
PBLUP model: the conventional breeding value is estimated by a single-trait animal model:

$$y = Xb + Zu + e$$

wherein y is a vector of phenotypic value, X is a design matrix for fixed-effect, b is a vector of fixed-effect including generation (birth year), hatching batch and gender, Z is a correlation matrix for random effect, u is a vector of breeding value and assumed to follow $u \sim N(0, A\sigma_u^2)$, wherein A is a matrix for molecular blood relationship, $\sigma_u^2$ is an additive genetic variance, e is a vector of residual and assumed to follow $e \sim N(0, I\sigma_e^2)$, wherein I is a identity matrix, and $\sigma_e^2$ is a residual variance.

ssGBLUP model: the ssGBLUP model is similar in form to the PBLUP model. The difference lies in that: the vector of random effect in the ssGBLUP model follows $u \sim N(0, H\sigma_u^2)$, wherein H is a matrix that integrates pedigree information and genomic information (Christensen and Lund, 2010; Legarra, et al., 2009). The H matrix is constructed as follows:

$$H = \begin{pmatrix} H_{11} & H_{12} \\ H_{21} & H_{22} \end{pmatrix} = \begin{pmatrix} A_{11} + A_{22}^{-1}(G - A_{22})A_{22}^{-1}A_{21} & A_{12}A_{22}^{-1}G \\ GA_{22}^{-1}A_{11} & G \end{pmatrix}$$

The subscripts 1 and 2 represent individuals without genotypes and individuals with genotypes, respectively. The inverse matrix of the H matrix is quite simple in form (Aguilar, et al., 2010):

$$H^{-1} = A^{-1} + \begin{bmatrix} 0 & 0 \\ 0 & G^{-1} - A_{22}^{-1} \end{bmatrix}$$

(4) Results:

TABLE 2

Comparison of accuracy of different genetic evaluation methods

| Traits | PBLUP | SSGBLUP |
|---|---|---|
| Weight at 28 weeks of age | 0.19 | 0.29 |
| Egg weight at 28 weeks of age | 0.17 | 0.30 |
| Number of eggs laid at 38 weeks of age | 0.22 | 0.38 |

(5) It can be seen that, compared with traditional selection methods, the use of the chip of the present invention for genomic selection can effectively improve the accuracy of genetic evaluation.

INDUSTRIAL APPLICABILITY

The SNP loci on the egg-type chicken whole-genome SNP chip provided by the present invention are respectively derived from 14,624 SNP loci shared by various line of major egg-type chicken breeds in China; 3,677 SNP loci related to disease-resistant traits in egg-type chickens; 16,000 SNP loci associated with economic traits of egg-type chickens; and 9,358 SNP loci for making up the genomic region that are not covered by the aforementioned probes. The 43,681 SNPs on the egg-type chicken whole-genome SNP chip of the present invention have DNA sequences as represented by SEQ ID NOs. 1 to 43681. The chip can specifically identify the genetic relationship between commercial egg-type chickens and local egg-type chicken breeds, and can also be used to perform applications such as genome-wide association analysis, genomic selection, QTL mapping for target traits, and population genetic analysis. The chip has versatility for domestic and abroad chicken breeds, can help accelerate the rapid development of the egg-type chicken industry, and has great economic and practical value and scientific research value.

SEQUENCE LISTING

The patent contains a lengthy sequence listing. A copy of the sequence listing is available in electronic form from the USPTO web site (https://seqdata.uspto.gov/?pageRequest=docDetail&DocID=US12275987B2). An electronic copy of the sequence listing will also be available from the USPTO upon request and payment of the fee set forth in 37 CFR 1.19(b)(3).

What is claimed is:

1. An egg-type chicken whole-genome single nucleotide polymorphism chip comprising 43,681 nucleic acid molecules comprising SEQ ID Nos 1-43,681.

* * * * *